(12) United States Patent
Yan

(10) Patent No.: US 6,743,189 B1
(45) Date of Patent: Jun. 1, 2004

(54) WIRE-SUPPORTING DIGITAL SPLINT

(76) Inventor: Joyce Cheuk-Kwan Yan, 38623 Cherry La., #128, Fremont, CA (US) 94536

( * ) Notice: Subject to any disclaimer, the term of this patent is extended or adjusted under 35 U.S.C. 154(b) by 0 days.

(21) Appl. No.: 10/460,948

(22) Filed: Jun. 13, 2003

(51) Int. Cl.[7] ................................................. A61F 5/00
(52) U.S. Cl. ........................................... 602/20; 602/22
(58) Field of Search ............................. 602/20, 21, 22, 602/30; 128/880, 878, 879; 604/289, 290, 292, 293, 304, 308; 606/53, 54, 59

(56) References Cited

U.S. PATENT DOCUMENTS 2,646,794 A * 7/1953 Baer
6,102,878 A * 8/2000 Nguyen ........................ 602/5
6,183,452 B1 * 2/2001 Bodmer et al. ............... 602/22
2003/0078531 A1 * 4/2003 Nguyen ...................... 602/22

* cited by examiner

Primary Examiner—Michael A. Brown
(74) Attorney, Agent, or Firm—Sierra Patent Group, Ltd.

(57) ABSTRACT

A digital splint has a base, a bracket, an access shaft, and a secure shaft. The base is configured to support a digit and the base has a length greater than its width. The bracket can be coupled to the base. The bracket has a first, second, and third walls. The second and third walls extend outward from the first wall. The access shaft is in the first wall and is disposed to receive a skin-penetrating device. The secure shaft is located within the first wall and is disposed at an angle to the access shaft. The secure shaft is coupled to the access shaft and is disposed to secure the skin-penetrating device through the access shaft.

20 Claims, 2 Drawing Sheets

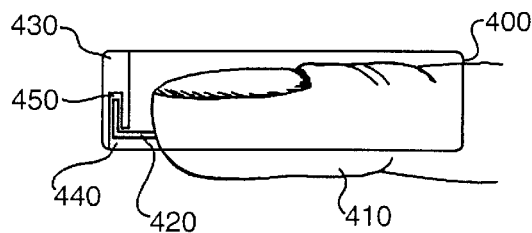

FIG. 4

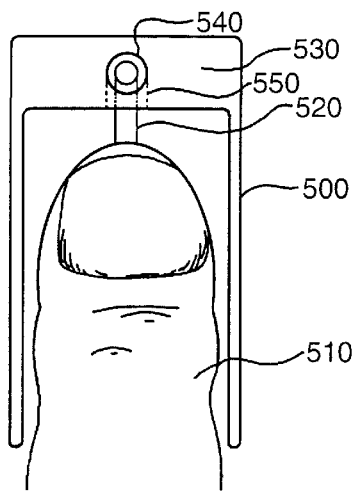

Protect the digit with a bracket, the bracket having a first, second, and third walls, the second and third walls extending outward from the first wall, an access shaft in the first wall, the access shaft disposed to receive a skin-penetrating device, a secure shaft located within the first wall and disposed at an angle to the access shaft, the secure shaft coupled to the access shaft and disposed to secure the skin-penetrating device through the access shaft.

610 — Secure the bracket to the digit.

FIG. 6

WIRE-SUPPORTING DIGITAL SPLINT

BACKGROUND OF THE INVENTION

1. Field of the Invention

Generally, the invention relates to a splint for toes or fingers in need of repair and support. More specifically, the invention is a splint for supporting toes or fingers having a protruding skin-penetrating device, for example a wire, in order to protect the digit, limit movement of the wire, hold the digit in the desired position, and reduce the risk of infection.

2. The Prior Art

When a toe or a finger is injured, the most common medical practice would be to "buddy splint" the wounded digit to an adjacent digit with sturdy tape. This method allows the adjacent digit to act as a splint in immobilizing the injured digit. This immobilization prevents further exacerbation of the injury and allows tissues to heal in the desired position. If an injury or deformity is severe enough, physicians and surgeons may elect to undergo surgical correction. The most common and one of the most economical practices after surgical correction of a digit is to insert a stainless steel wire, known as a K-wire, into the digit to hold the digit in its desired position during the recuperation period. The K-wire exits at the tip of the digit and it functions to splint the digit and hold it in a desirable position during recovery. The K-wire is bent at one end in order to assist in removal and prevent the wire from being accidentally pushed into the digit. The K-wire is later removed after healing.

Commonly, a plastic end cap is placed on the very tip of a wire in a digit with an external fixation wire. The plastic cap prevents the sharp edges of the tip of the K-wire from injuring the patient or the treating clinicians, however the end cap does not prevent retraction of the K-wire from the patient's digit nor does it prevent the external portion of the K-wire from being pushed further into the patient's digit, which are the most commonly seen consequences of current practice of placement of these plastic end caps. Numerous attempts have been made in the past by various authors in attempting to splint a toe or finger in its post-surgical or injured state. These include devices made from various materials and of various designs. One problem with the prior art is that it fails to provide support and protection specifically for a digit with a protruding, skin-penetrating device.

U.S. Pat. No. 6,183,452, entitled Aseptic Protector For Skin Penetrating Devices, makes an attempt to address these issues. Nonetheless, the aseptic protector's design is flawed. The preferred shape of the aseptic protector is cylindrical and therefore encloses the digits medially, laterally, dorsally, and plantarly. This is a poor design for injured digits either traumatic, as in an accident, or in a post-surgical environment where digits will physiologically tend to swell. The tubular design will strangulate and further cause damage to an already injured digit that will tend to swell. Additionally, by surrounding the digit, the tubular aseptic protector will prevent the patients from looking at the digit to assess the vascular status.

BRIEF DESCRIPTION OF THE INVENTION

A wire-supporting, digital splint has a base, a bracket, an access shaft, and a secure shaft. The base is configured to support a digit and the base has a length greater than its width. The bracket can be coupled to the base. The bracket has a first, second, and third walls. The second and third walls extend outward from the first wall. The access shaft is in the first wall and is disposed to receive a skin-penetrating device. The secure shaft is located within the first wall and is disposed at an angle to the access shaft. The secure shaft is coupled to the access shaft and is disposed to secure the skin-penetrating device through the access shaft.

Furthermore, while the invention is described herein as utilized on toes and fingers, it will be appreciated that the present invention is not so limited. Splint devices in accordance with the principles of the present invention may be utilized on other body parts whose shape and conformation are adaptable for such use.

The current invention address the shortcomings of the prior art while protecting the external portion of the skin-penetrating device from being pulled from or pushed into the digit. Also, the sharp edges of the distal tip of the skin-penetrating device is completely enclosed within a wall of the bracket so it will not pose as a hazard to either the treating personnel or the patient.

BRIEF DESCRIPTION OF THE DRAWING FIGURES

FIG. 4 is an elevation view illustrating one embodiment of the invention implemented with a finger.

FIG. 5 is a plan view illustrating one embodiment of the invention implemented with a toe.

FIG. 6 is a flow diagram illustrating a method of implementing the digital splint.

DETAILED DESCRIPTION OF THE INVENTION

The following description of the invention is not intended to limit the scope of the invention to these embodiments, but rather to enable any person skilled in the art to make and use the invention.

Figure 1:
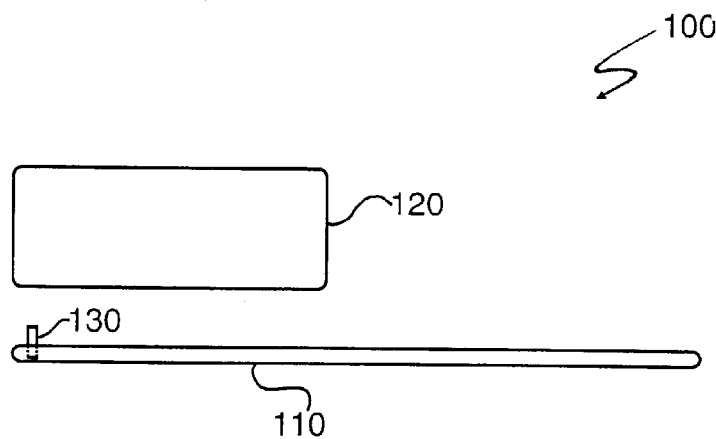
FIG. 1 is an elevation view illustrating one embodiment of a wire-supporting digital splint.

FIG. 1 is a plan view illustrating one embodiment of a wire-supporting digital splint. Splint 100 includes base 110 and bracket 120. Base 110 supports one or more digits, for example fingers or toes, and provides stability and protection after an injury or post-surgery. Base 110 has guide post 130, which may be inserted into base 110 and held, for example, by pressure or adhesive, or guide post 130 may be an integral part of base 110. In one embodiment, guide post 130 protrudes from base 110 by approximately one-quarter of the height of the bracket. In one embodiment, base 110 has two guide posts, though base 110 may have a greater or lesser number. In one embodiment, base 110 is 0.09 inches, or 2 mm, thick.

Bracket 120 couples to base 110. Bracket 120 has three walls configured in a U-shape and serves to secure and protect the medial, lateral, and distal aspects of a digit. FIG. 1 illustrates only a single side of bracket 120. Bracket 120 may have one or more holes (not shown) configured to receive guide post 130. In one embodiment, bracket is 0.6 inches, or 1.5 cm, high and 1.38 inches, or 4 cm, long, and 2.3 cm in width in order to accommodate a lesser or middle toe. The size and shape of the wire-supporting digital splint may be configured to accommodate any digit of any size. For example, a big toe measuring 4 cm in length by 3 cm in width by 2.5 cm in height could be accommodated by a splint comprised of a base with dimensions of 10 cm in length by 4 cm in width by 0.2 cm in height and a bracket of 5 cm in length by 4 cm in width by 3.5 cm in height. A small toe measuring 2.5 cm in length by 1.5 cm in width by 1.5 cm in height could be accommodated by a splint comprised of a base in the dimensions of 7 cm in length by 2 cm in width by 0.2 cm in height and a bracket of 3 cm in length by 2 cm in width by 1.5 cm in height. A finger measuring 7.5 cm in length by 1.5 cm in width by 2 cm in height could be accommodated by a splint comprised of a base measuring 15 cm in length by 2.2 cm in width by 0.2 cm in height and a bracket measuring 8 cm in length by 2.2 cm in width by 1.5 cm in height.

In another embodiment, base 110 and bracket 120 are secured together without a guide post. In another embodiment, base 110 and bracket 120 are integral to one another, therefore having no need of a means to secure them.

Figure 2:
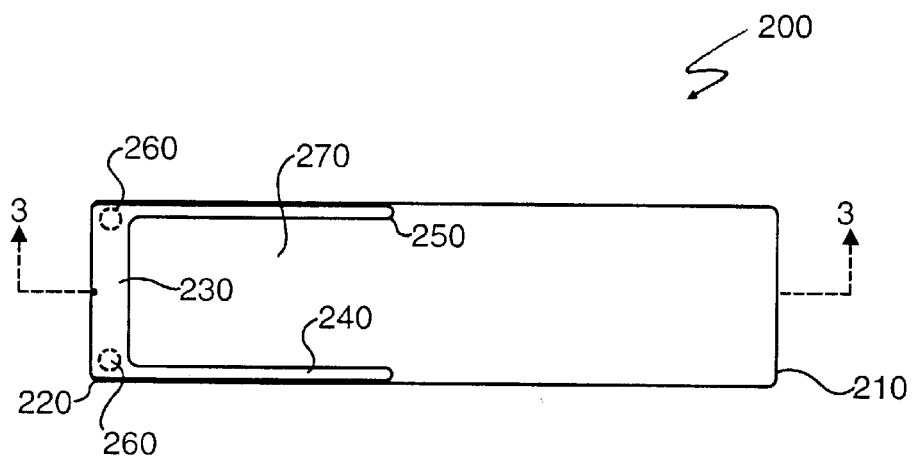
FIG. 2 is a plan view illustrating one embodiment of a wire-supporting digital splint.

FIG. 2 is a plan view illustrating splint 200, which is splint 100 from FIG. 1. Splint 200 includes base 210 and bracket 220. In one embodiment, base 210 is 0.9 inches wide and 3.5 inches long.

Bracket 220 is positioned, in this example, above and aligned with base 210. Bracket 220 has first wall 230, second wall 240 and third wall 250. In one embodiment, bracket 220 is 0.9 inches, or 2.3 cm, wide, with first wall 230 having a thickness of 0.2 inches, or 0.5 cm, while second wall 240 and third wall 250 have a thickness of 0.1 cm. Bracket 220 has within it holes 260 in order to receive guide posts (see FIG. 1). Bracket 220 may have more or fewer holes. Bracket 220 has bracket interior 270, which is surrounded by first wall 230, second wall 240 and third wall 250.

Figure 3:
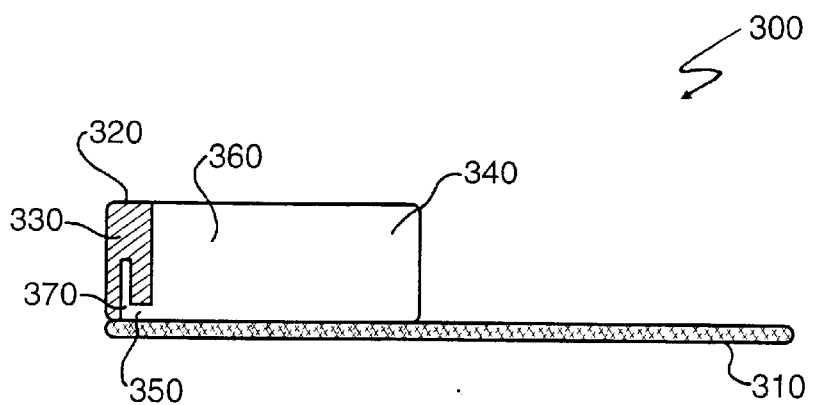
FIG. 3 is a sectional view from FIG. 2, illustrating a cross-sectional view of the invention.

FIG. 3 is a sectional view of FIG. 2, illustrating a cross-sectional view of splint 200. Splint 300 includes base 310 and bracket 320. Bracket 320 includes first wall 330 and third wall 340. Inside of first wall 330 is access shaft 350 leading from bracket interior 360 (also see bracket interior 270 from FIG. 2) to secure shaft 370. In one embodiment, secure shaft 370 and access shaft 350 are perpendicular to one another, though they may be at any angle to one another.

Secure shaft 370 is within first wall 330 and is configured to receive the bent end of a skin-penetrating device such as a K-wire. Typically a K-wire is inserted into a digit in order to promote bone and/or soft tissue alignment. A portion of the K-wire exits the digit and is bent at an angle in order to prevent the wire from being pushed into the digit. The bent portion of the K-wire (see FIGS. 4 and 5) is inserted into secure shaft 370, while access shaft 350 contains a part of the straight portion that extends from the digit. Access shaft 350 may be at any height within first wall 330. The digit will typically rest within bracket interior 360. Secure shaft 370 is typically located within the center of first wall 330 and extended as shown in FIG. 3, although secure shaft 370 may have any orientation, position, or shape such that first wall 330 may accommodate it.

K-wires and other skin-penetrating devices have diameters on the order of approximately 0.028 inches to approximately 0.054 inches. In one embodiment, secure shaft 370 has a diameter of 0.062 inches in order to accommodate the largest K-wire. However, secure shaft 370 may have a smaller diameter in order to more closely secure a smaller fixation tool such as a stainless steel wire or a larger diameter in order to fit a larger fixation tool such as a Steinman Pin. In one embodiment secure shaft 370 has a length 0.4 inches, although the length of secure shaft 370 may be any length (or height) as long as it does not exit first wall 330. In another embodiment, secure shaft 370 exits first wall 330.

FIG. 4 is a diagram illustrating one embodiment of bracket 400 implemented with finger 410. Finger 410 has a skin-penetrating device, or K-wire 420, extending from it. K-wire 420 fits through first wall 430 and into access shaft 440 and secure shaft 450. In this embodiment, K-wire 420 extends from finger 410 and is bent upward at a ninety-degree angle. Therefore access shaft 440 and secure shaft 450 are at a ninety-degree angle to one another. In another embodiment, a K-wire could bend at any other angle, and could also bend in any other direction than that shown in FIG. 4, for example to the side or downward. A bracket could still contain a differently bent K-wire, the bracket having appropriate dimensions in order to accommodate the K-wire within the access shaft and the secure shaft. FIG. 4 illustrates the usage of the wire supporting digital splint without the base as one embodiment of the invention. The splint may be secured to the digit by using, for example, bandaging material such as gauge, Kling, Kerlix, Coban, etc.

FIG. 5 is a plan view illustrating one embodiment of the bracket implemented with a toe. Bracket 500 encloses toe 510 with protruding K-wire 520. First wall 530 houses secure shaft 540, K-wire 520, and access shaft 550. In one embodiment, access shaft 550 and secure shaft 540 closely secure K-wire 520. In another embodiment, access shaft 550 and secure shaft 540 loosely secure K-wire 520. In one embodiment, the secure shaft extends to the top of the first wall, as illustrated in FIG. 5. In another embodiment, the secure shaft extends only partially through the first wall, as illustrated in FIG. 3.

FIGS. 4 and 5 illustrate that the U-shaped bracket surrounds the digit over several, though not all of its surfaces. With the base in place, each of the digits in FIGS. 4 and 5 would have their top surfaces exposed and free for inspection or to allow for swelling.

FIG. 6 is a flow diagram illustrating a method of implementing the digital splint. In block 600, protect the digit with a bracket, the bracket having a first, second, and third walls, the second and third walls extending outward from the first wall, an access shaft in the first wall, the access shaft disposed to receive a skin-penetrating device, a secure shaft located within the first wall and disposed at an angle to the access shaft, the secure shaft coupled to the access shaft and disposed to secure the skin-penetrating device through the access shaft. In block 610, secure the bracket to the digit. The bracket may be secured to the digit by a medium, for example gauze or tape.

In one embodiment the digital splint is molded from a hard plastic, for example a polycarbon. In whatever material the splint is molded from, whether plastic, metal, or glass, the digital splint should be able to be autoclaved or be able to be sterilized in accordance with guidelines established and published by the U.S. Environmental Protection Agency, for use in an intra-operative or post-operative setting where such sterilization process provides patient safety.

In another embodiment the digital splint is molded as a single piece, without a distinct and separate base and bracket.

The digital splint may provide support and protection to a damaged digit regardless of whether a K-wire protrudes from the digit. Additionally, the base and bracket may be malleable, in order to conform to the digit. The malleability may be heat induced or be present at room temperature. The invention may also serve as both a toe guard and as a finger splint. In addition, when constructed in various sizes, the present invention is suitable for all digits and not just for a particular outer digit, such as the big toe/thumb or the little toe/finger, or the middle digits, such as the index, middle, or ring finger/toe. Furthermore, the digital splint allows swelling of the digit without constriction and a visual examination of the digit to determine drainage or infection.

As any person skilled in the art will recognize from the previous description and from the figures and claims, modifications and changes can be made to the embodiments of the invention without departing from the scope of the invention defined in the following claims.

What is claimed is:

1. A digital splint comprising:
   a bracket configured to surround a digit, the bracket having a first, second, and third walls, the second and third walls extending outward from the first wall;
   an access shaft in the first wall, the access shaft disposed to receive a skin-penetrating device; and
   a secure shaft located within the first wall and disposed at an angle to the access shaft, the secure shaft coupled to the access shaft and disposed to secure the skin-penetrating device through the access shaft.

2. The digital splint of claim 1 further comprising:
   a base configured to support the digit, the base having a length greater than its width, wherein the bracket is configured to be coupled to the base.

3. The digital splint of claim 2, wherein the base further comprises at least one guide post configured to align the base and the bracket.

4. The digital splint of claim 3 wherein the bracket has at least one hole configured to receive the guide post.

5. The digital splint of claim 4, wherein the base is longer than the bracket.

6. The digital splint of claim 3, wherein the secure shaft and the access shaft are approximately perpendicular to each other.

7. The digital splint of claim 6, wherein the secure shaft is approximately orthogonal to a plane defined by the base.

8. The digital splint of claim 1, wherein the second wall is parallel to the third wall, and the first wall, second wall and third wall are configured in a "U" shape.

9. The digital splint of claim 1 wherein the bracket is configured to surround the digit over a portion and not all of the digit's surfaces.

10. A digital splint comprising:
    a base configured to support a digit, the base having a length greater than its width;
    a bracket coupled to the base, the bracket having a first, second, and third walls, the second and third walls extending outward from the first wall;
    an access shaft in the first wall, the access shaft disposed to receive a skin-penetrating device; and
    a secure shaft located within the first wall and disposed at an angle to the access shaft, the secure shaft coupled to the access shaft and disposed to secure the skin-penetrating device through the access shaft.

11. The digital splint of claim 10, wherein the secure shaft and the access shaft are approximately perpendicular to each other.

12. The digital splint of claim 11, wherein the secure shaft is approximately orthogonal to a plane defined by the base.

13. The digital splint of claim 10, wherein the second wall is parallel to the third wall, and the first wall, second wall and third wall are configured in a "U" shape.

14. The digital splint of claim 13, wherein the base further comprises at least one guide post configured to align the base and the bracket.

15. The digital splint of claim 14 wherein the bracket has at least one hole configured to receive the guide post.

16. The digital splint of claim 15, wherein the base is longer than the bracket.

17. A digital splint comprising:
    a base configured to support a digit, the base having a length greater than its width and at least one guide post;
    a bracket configured to be coupled to the base by at least one hole in the bracket configured to receive the guide post, the bracket having a first, second, and third walls, the second and third walls extending outward from the first wall, the first wall, second wall and third wall configured in a "U" shape;
    an access shaft in the first wall, the access shaft disposed to receive a skin-penetrating device; and
    a secure shaft located within the first wall and approximately perpendicular to the access shaft, the secure shaft coupled to the access shaft and disposed to secure the skin-penetrating device through the access shaft, the secure shaft disposed at approximately a right angle to a plane defined by the base.

18. A method of splinting a digit comprising:
    protecting the digit with a bracket, the bracket having a first, second, and third walls, the second and third walls extending outward from the first wall, an access shaft in the first wall, the access shaft disposed to receive a skin-penetrating device, a secure shaft located within the first wall and disposed at an angle to the access shaft, the secure shaft coupled to the access shaft and disposed to secure the skin-penetrating device through the access shaft; and
    securing the bracket to the digit.

19. The method of claim 18 further comprising:
    stabilizing the digit with a base configured to support the digit and couple to the bracket, the base having a length greater than its width, and wherein securing the bracket to the digit comprises securing the bracket and the base to the digit.

20. The method of claim 19 wherein securing the bracket comprises wrapping a medium around the bracket and the digit such that the bracket is removeably attached to the digit and allows circulation.

* * * * *